United States Patent
Ernst et al.

(10) Patent No.: US 8,665,257 B2
(45) Date of Patent: *Mar. 4, 2014

(54) THREE-DIMENSIONAL MODELING OF THE ORAL CAVITY

(76) Inventors: Maurice Moshe Ernst, Jerusalem (IL); Micha Geffen, Gillon (IL); Uri Neta, Coranit (IL); Carmi Cohen, Tel Adashim (IL)

( * ) Notice: Subject to any disclaimer, the term of this patent is extended or adjusted under 35 U.S.C. 154(b) by 965 days.

This patent is subject to a terminal disclaimer.

(21) Appl. No.: 12/160,364

(22) PCT Filed: Jan. 11, 2006

(86) PCT No.: PCT/IL2006/000040
§ 371 (c)(1),
(2), (4) Date: Dec. 21, 2010

(87) PCT Pub. No.: WO2007/080563
PCT Pub. Date: Jul. 19, 2007

(65) Prior Publication Data
US 2011/0109616 A1    May 12, 2011

(51) Int. Cl.
*G06T 15/00*    (2011.01)

(52) U.S. Cl.
USPC .............................. 345/419; 345/424; 700/98

(58) Field of Classification Search
None
See application file for complete search history.

(56) References Cited

U.S. PATENT DOCUMENTS

| | | | |
|---|---|---|---|
| 6,621,491 B1 * | 9/2003 | Baumrind et al. | 345/419 |
| 7,027,642 B2 * | 4/2006 | Rubbert et al. | 382/154 |
| 7,330,577 B2 * | 2/2008 | Ernst et al. | 382/128 |
| 7,912,257 B2 * | 3/2011 | Paley et al. | 382/128 |
| 2001/0038705 A1 * | 11/2001 | Rubbert et al. | 382/128 |
| 2005/0219242 A1 * | 10/2005 | Anh et al. | 345/419 |

* cited by examiner

*Primary Examiner* — Said Broome (57) ABSTRACT

A method for creating three-dimensional models of intra-oral scenes features. The intra-oral scene is illuminated by a two-dimensional array of structured illumination points, with anti-aliasing achieved by using stored two-dimensional patterns of pixels for anti-aliasing. Using a single camera to form images reduces the amount of apparatus necessary to introduce into the patient's mouth. Three-dimensional models are obtained from the single image by triangulation with a stored image of the structured illumination onto a reference surface such as a plane. Alternative methods include the use of "bar-coded" one-dimensional patterns.

2 Claims, 6 Drawing Sheets

THREE-DIMENSIONAL MODELING OF THE ORAL CAVITY

FIELD OF THE INVENTION

The present invention relates to computerized modeling of three-dimensional objects, and, more particularly, to a system and method for three-dimensional modeling of intra-oral objects and features in dental applications.

BACKGROUND OF THE INVENTION

There is a need in dental medicine for making three dimensional (herein also denoted as "3D") models of internal scenes of the mouth. The term "intra-oral scene" herein denotes any collection of intra-oral objects, artifacts, surfaces, or features which can be visualized and modeled. Such models of intra-oral scenes can support various aspects of dental practice. A well-known illustration of the utility, effectiveness, and procedural and economic impact of automatic measuring and imaging techniques in dentistry involves the examination, charting, diagnosing, and treatment of dental patients who require prostheses such as crowns, bridges, dentures, or implants. Data and information obtained from measuring, imaging, and mapping intra-oral objects can be used to accurately and cost-effectively design, manufacture, fit, and monitor dental prostheses, thereby replacing currently-used inaccurate non-imaging techniques, which are labor-intensive and otherwise costly in materials and time. Automatic dental measuring and imaging techniques are also applicable for performing various types of restorative procedures, occlusal registration, and orthodontic and tempero mandibular joint (TMJ) dysfunction therapies.

Electro-optical techniques are often used in medical imaging because they are relatively inexpensive in capital outlay as well as in cost-per-use, and are perceived as being non-harmful to the patient. Such techniques, however, must be adapted to the particular circumstances and problems associated with dental imaging.

Important constraints in applying medical optical imaging to the dental field include:

space limitations—equipment must be compact enough to fit comfortably within the confines of the mouth;

time limitations—the image must be formed in a brief time to avoid problems of the movement of the patient as well as the movement of the practitioner and apparatus; and surface detail limitations—accurately plotting 3 surface contours of intra-oral scenes must take into account the absence or paucity of surface detail in many close-up applications, where only partial views of intra-oral features may be available.

Measuring the three-dimensional distribution and mapping of intra-oral objects, has been implemented by using various methods. Typical intra-oral objects and features include, but are not limited to a part or entirety of any combination of: teeth; gum; intra-oral soft tissue; bone matter; dental undercuts; dental fixtures and dental prostheses of any kind, permanent or removable, which are located inside the oral cavity. Specific intra-oral objects and features can be measured, for example, as disclosed in U.S. Pat. No 6,402,707 to Ernst, one of the present inventors, pertaining chiefly to dental applications. In the present application, many well-known methods can be used for producing a compound database which can be stored in a computer to serve as reference for consequent medical procedures.

In practice, a limitation is imposed by the lack of recognizable surficial surgical features on intra-oral objects. This limitation is often encountered in situations in which a surface is to be sampled three dimensionally for 3D modeling. There are a variety of known techniques to compensate for inadequate quantitative and qualitative surface details. These techniques for improving the acquisition of surface details, include (either separately or combined): spraying the surface of the object to be imaged with powder to improve optical properties for imaging; and projecting and/or diffracting structured illumination patterns and observing their deformation.

Several methods have been disclosed for producing maps or three-dimensional distribution models of surficial features. For example, active triangulation is a specific method that uses an active light spot and several cameras for measuring the distribution of objects on a surface. Scanning the active light spot can produce a whole map of a surface. Photogrammetry is a discipline in which analytic methods are applied for extracting three-dimensional information from photographs. Photogrammetry, as well as any discipline based on images, extends easily to map production because of the range of information obtained by the cameras employed.

As suggested above, it is well-known that making three-dimensional measurements of an intra-oral scene for the purpose of electronically constructing a model of the distribution of features, can be achieved by obtaining multi-view images of the intra-oral scene and subsequently applying appropriate analytical algorithms to the images. At least two images of the same intra-oral scene are acquired from different viewing angles. Matching features in the intra-oral scene are searched in the corresponding images. To calculate the relative height (z-dimension) of a feature, the parallax between matching appearances of the feature in different images of the same intra-oral scene is calculated via triangulation, from which the distance of the feature from a reference point is computed. Several common techniques for increasing the distinctness of the features in the images are discussed below.

Figure 1:
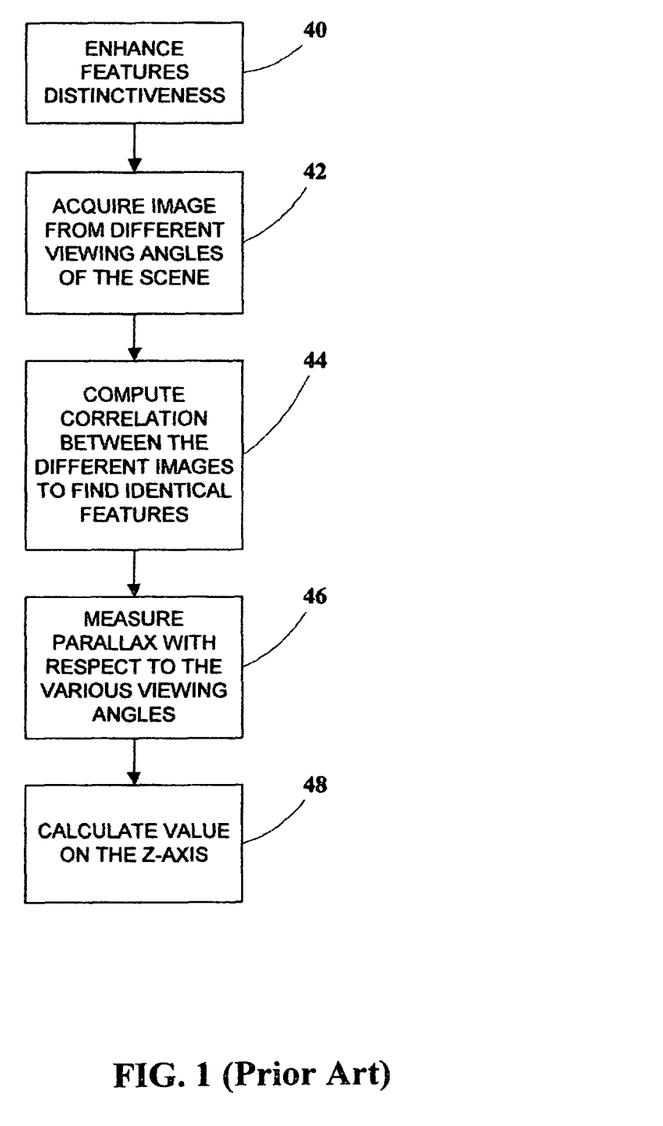
FIG. 1 is a flow-chart of a prior art method for three dimensional modeling of an intra-oral scene using multi-view imagery.

FIG. 1, to which reference is now made, is a flow-chart describing the order of steps that takes place in the course of a common prior-art three-dimensional modeling of a site of interest. In a step 40 the distinctiveness of features in the intra-oral scene is enhanced. In a step 42 images are acquired of the site of interest at different angles. In a step 44 matching is accomplished between features at the different images acquired. In a step 46 the parallax is measured for identical features in different images. In a step 48 the values on the z-axis are calculated for the identified features. A 3D map, or model, can then be compiled, describing the distribution of the identified features in the xyz-space.

As previously noted, however, a significant limitation in dental work is the lack of surface detail in many situations. Without a substantial amount of surface detail, it is not possible to unambiguously match surface features for accurate triangulation. To solve this problem, instead of illuminating the intra-or scene uniformly and trying to match features through complex pattern-recognition algorithms, a well-known method is to scan a beam of light across the intra-oral scene to create an array of highlighted lines or points. This "structured illumination" can then be used for matching features in the triangulation previously mentioned. The resulting 3D model is a "wire mesh" or "polyhedral" model of the intra-oral scene. This is an advantageous approach, because the resolution of the model can be easily varied by changing the density of the scanned lines or points over the intra-or scene, and for many intra-oral scenes of interest, the regions between e lines or points (which are not illuminated by the structured illumination) can be approximated through various smoothing functions. The result is a model of adjustable accuracy which can be analyzed using relatively simple algorithms.

Unfortunately, however, scanning (which is essentially a one-dimensional, or "1D" approach) can sometimes require excessive time, particularly if high resolution is desired. In contrast, imaging (which is a two-dimensional, or "2D" approach) can capture a much greater amount of information in the same time—or, alternatively, can capture the same amount of information in a much smaller time. This factor is important when considering the above-mentioned time limitation, in order to reduce the detrimental effects of patient, practitioner, and apparatus movement.

U.S. Pat. No. 4,687,325 to Corby (herein denoted as "Corby") notes that it is also possible to employ structured illumination using a single image of the intra-oral scene, whereby the triangulation is performed relative to a stored image (or the data corresponding thereto) of the structured illumination as projected on a plane or other surface of known curvature. Corby, however, is limited to the use of a one-dimensional scanning methodology, which (as discussed above) may not be suitable for certain dental applications because of the patient/practitioner movement that is likely to be encountered. Hans-Gerd Maas in *International Archives of Photogrammetry and Remote Sensing* Vol. XXIX part B5, pages 709-713 (1992), the contents of which article are incorporated by reference for all purposes as if set forth fully herein, likewise teaches the use of a perfect grid projected on a close object whose surface is to be computed. The projected grid deviates from its original form at the surface from which it reflects, and those deviations from the perfect grid are used to compile the three-dimensional model for the reflective surface. A limitation associated with the employment of regular grids is that of discontinuities and ambiguities. In the case of a discontinuity, a broken grid appearing over the reflecting surface is caused by the discontinuous relief. Broken grid lines are a cause for errors because of the ambiguities introduced by this phenomenon.

Other prior art includes U.S. Pat. No. 4,952,149 to Duret et al. (herein denoted as "Duret"), wherein a method and apparatus is disclosed for taking impressions of a portion of the body which utilizes the projection of a grid of sinusoidal profile onto the body portion of which the impression is to be taken. In U.S. Pat. No. 4,964,770 to Steinbichler et al. (herein denoted as "Steinbichler"), a process is disclosed for making artificial teeth, where horizontal or other contour lines are generated on the ground tooth stump and on adjacent surfaces to create a three-dimensional map. Three-dimensional reconstruction is achieved by the use of interferometry, moiré, and laser scanning methods. In U.S. Pat. No. 5,372,502 to Massen et al. (herein denoted as "Massen 502"), an invention is based on calculating a topographic representation by comparing between a digital image of known pixel detail projected onto a tooth surface and the resulting distorted image reflected off the tooth surface, in accordance with moiré, phase-shift, triangulation, and photogrammetry techniques. Through a comparison between the undistorted pattern projected by the probe and the distorted pattern reflected from the specific area within the oral cavity, topographical information of the imaged teeth is obtained. In U.S. Pat. No. 5,386,292 to Massen et al. (herein denoted as "Massen '292"), an invention is described of an error factor that corrects image distortions due to factors such as enamel translucency. In U.S. Pat. No. 6,529,627 to Callari, et al., by a system is described that uses structured illumination that is manually projected on an object and by deriving the 3D model by integrating the 3D data into the initial 3D model.

One of the recognized problems in using structured light in lines or points is that of aliasing, or false matching of the structured illumination. A plain point of light is normally indistinguishable from other plain points of light, and so there can arise ambiguities in matching the same point from one image to another. If two different points are mistakenly matched when triangulating different images, the resulting z-axis calculation will be in error, and the 3D model will be defective. (The same problem applies to the use of lines.) In real-time scanning using electronic imaging, synchronizing the output from the different image sensors serves as an anti-aliasing mechanism. However, this cannot be employed for projected (non-scanned) images or for stored images where features are matched after the structured illumination has been projected, because there is no timing information. It also cannot be used with the single imaging method mentioned above. Several anti-aliasing methods, using different schemes of encoding the structured illumination, are described in Corby. Some of these methods involve modulating the structured illumination in wavelength and/or intensity. Corby's own method involves encoding spatially-modulated predetermined patterns in the scanned light, which can be unambiguously matched in the different images.

Once again, the time limitation presented above is noted for dental applications. In particular, certain prior art schemes would require illuminating the same areas of the intra-oral scene with patterns over a prolonged time period or repeatedly at different times. These practices, however, can introduce inaccuracies in the measurements due to any relative movement between the dental patient, the apparatus that projects the illumination, and the apparatus that captures the images (camera). This condition is exacerbated if the apparatus is being held or manipulated by the dental practitioner, because in this case there is an additional source of movement involved.

U.S. Pat. No. 6,167,151 to Albeck, et al. (herein denoted as "Albeck '151") discloses a means of creating a spatially-modulated random pattern by the phenomenon of laser speckle, which can then be used in a similar manner to the predetermined patterns of Corby, for identifying corresponding points in multiple images. An advantage of random patterns over predetermined patterns in anti-aliasing is that certain random systems can mathematically generate a large number of distinct patterns easily, whereas systems of distinct predetermined patterns are generally more restricted and thus limited in number. On the other hand, however, predetermined patterns (such as in Corby) can be set up in advance to be absolutely distinguishable. Random patterns, in contrast, are not predetermined, and therefore may exhibit some similarities among themselves. The patterns of Albeck '151, for example, which depend on the interference properties of coherent light upon uneven surfaces, are probabilistic and therefore different patterns can be similar in appearance, even though this is unlikely. The anti-aliasing of Albeck '151, therefore, is statistical rather than absolute.

A principal limitation of Albeck '151 is that the random patterns, being created by a physical process (laser speckle), can be neither stored nor reproduced. This requires that the multiple images of the intra-oral scene under the structured illumination be captured simultaneously in order that the same random speckle patterns be included in the different images. The fact that the random patterns of Albeck '151 cannot be stored or reproduced also precludes using a single image of the intra-oral scene under the structured illumination which is later referenced to a previously-stored image of the structured illumination impinging on a known surface, such as a planar surface (previously noted to have been described in Corby).

As noted above, an important limitation is imposed by the small space inside the mouth, which does not permit the introduction of bulky apparatus. In particular, it would be highly advantageous to use only a single imaging sensor (producing a single image or single projection) to capture the structured illumination patterns on the intra-oral features for comparison with the recorded structured illumination patterns on a known surface. Doing so would significantly reduce the amount of apparatus placed in the mouth and be responsive to the space limitation of dental applications, as previously noted. Furthermore, it would be desirable to employ an imaging, rather than a scanning technique, to eliminate problems caused by movement of the patient and/or the practitioner.

There is thus a need for, and it would be highly-desirable to have, a system and method for use in three-dimensional modeling of intra-oral features in dental applications that provides compact apparatus for use in the confines of the mouth, simultaneous acquisition of three-dimensional information over the entire intra-oral scene to eliminate problems caused by patient and/or practitioner movement, and the ability to extract three-dimensional information from partial scenes which do not have large amounts of surface detail. These goals are met by the present invention.

SUMMARY OF THE INVENTION

It is a goal of the present invention to facilitate 3D intra-oral modeling for dental applications while requiring minimal apparatus to be placed inside the mouth.

It is also a goal of the present invention to facilitate 3D in intra-oral modeling for dental applications without relying on surface detail of the objects to be modeled, where only partial views of intra-oral features may be available.

It is a further goal of the present invention to minimize or eliminate the effect of movement of the patient, the practitioner, and the apparatus during the procedure of 3D intra-oral imaging for dental applications. To attain these goals, the present invention utilizes a single camera (or "visual sensor") to produce an image of an intra-oral scene, such that the image contains 3D information about the surface of the intra-oral features to be modeled.

To obtain the "z" information for three-dimensional modeling, the intra-oral scene is illuminated, during the acquiring of the image by the camera, by a two-dimensional image of structured illumination projected from a first angle with respect to the intra-oral scene. Then the camera is positioned at a second angle with respect to the intra-oral scene, to produce a normal image containing two-dimensional "x-y" information as seen at that second angle. The structured illumination projected from a photographic slide superimposes a two-dimensional array of patterns over the intra-oral scene and appears in the captured image. The "z" information in the intra-oral scene is then recovered from the camera image of the scene under the structured illumination by performing a triangulation of each of the patterns in the array on the single image with reference to an image of the structured illumination projected on a reference plane, which was also illuminated from the first angle.

In order to unambiguously match corresponding points in the image of the intra-oral scene and in the stored image, the points of the structured illumination are spatially-modulated with two-dimensional random patterns which have been generated and saved in a projectable medium, a non-limiting example of which is a photographic slide. Unlike the prior-art random patterns of Albeck '151, the random patterns of the present invention are reproducible, so that the patterns projected onto the intra-oral scene to be imaged are the same as the corresponding patterns in the saved image. Furthermore, unlike the prior-art patterns of Corby, which are one-dimensional, the patterns of certain preferred embodiments of the present invention are two-dimensional.

Therefore, according to a first aspect of the present invention there is provided a method for three-dimensional modeling of the surface features of a intra-oral scene for a dental application, the method including: (a) generating a two-dimensional array of a plurality of random two-dimensional patterns; (b) saving the array in a projectable medium; (c) projecting the array from the projectable medium onto a reference surface from a first angle; (d) acquiring a first image of the array projected on the reference surface, wherein the acquiring the first image is performed from a second angle; (e) projecting the array from the projectable medium onto the intra-oral scene the first angle; (f) acquiring a second image of the array projected on the intra-oral scene from the second angle; (g) calculating the two-dimensional relative positions of the random patterns based on the relative positions thereof in an image; (h) matching the random two-dimensional patterns in the first image with the random two-dimensional patterns in the second image; (i) calculating the parallax between the random patterns in the first image with the random patterns in the second image; (j) calculating a three-dimensional relative positions of the random patterns based on the two-dimensional relative positions and the parallax; and (k) constructing a three-dimensional model of the intra-oral scene based on the three-dimensional relative positions.

In a second aspect of the present invention there is provided a method for three-dimensional modeling of the surface features of a intra-oral scene for a dental application, the method including: (a) generating a two-dimensional array of a plurality of random one-dimensional patterns; (b) saving the array in a projectable medium; (c) projecting the array from the projectable medium onto a reference surface from a first angle; (d) acquiring a first image of the array projected on the reference surface, wherein the acquiring the first image is performed from a second angle; (e) projecting the array from the projectable medium onto the intra-oral scene the first angle; (f) acquiring a second image of the array projected on the intra-oral scene from the second angle; (g) calculating the two-dimensional relative positions of the random patterns based on the relative positions thereof in an image; (h) matching the random one-dimensional patterns in the first image with the random one-dimensional patterns in the second image; (i) calculating the parallax between the random patterns in the first image with the random patterns in the second image; (j) calculating a three-dimensional relative positions of the random patterns based on the two-dimensional relative positions and the parallax; and (k) constructing a three-dimensional model of the intra-oral scene based on the three-dimensional relative positions.

In a third aspect, the present invention is directed to providing a system for three-dimensional modeling of the surface features of an intra-or scene for a dental application, the system comprising:

a two-dimensional array of a plurality of random two-dimensional patterns;

a storage medium for said array, said storage medium operative to allow projecting said array;

a first image of said array projected on a reference surface a projector for projecting said array from said storage medium onto the intra-oral scene at a first angle;

an acquiring means for acquiring a second image of said array projected on the intra-oral scene from a second angle;
a first position calculator for calculating the two-dimensional relative positions of said random patterns based on the relative positions thereof in an image;
a pattern-matching means for matching said random two-dimensional patterns in said first image with said random two-dimensional patterns in said second image;
a parallax calculator for calculating the parallax between said random patterns in said first image with said random patterns in said second image;
a second position calculator for calculating a three-dimensional relative positions of said random patterns based on said two-dimensional relative positions and said parallax; and
a modeling means for constructing a three-dimensional model of the intra-oral scene based on said three-dimensional relative positions.

In a fourth aspect, the present invention is directed to providing a system for three-dimensional modeling of the surface features of an intra-oral scene for a dental application, the system comprising:
two-dimensional array of a plurality of random one-dimensional patterns;
a storage medium for said array, said storage medium operative to allow projecting said array;
a first image of said array projected on a reference surface
a projector for projecting said array from said storage medium onto the intra-oral scene at a first angle;
an acquiring means for acquiring a second image of said array projected on the intra-oral scene from a second angle;
a position calculator for calculating the two-dimensional relative positions of said random patterns based on the relative positions thereof in an image;
a pattern-matching means for matching said random one-dimensional patterns in said first image with said random one-dimensional patterns in said second image;
a parallax calculator for calculating the parallax between said random patterns in said first image with said random patterns in said second image;
a position calculator for calculating a three-dimensional relative positions of said random patterns based on said two-dimensional relative positions and said parallax; and
a modeling means for constructing a three-dimensional model of the intra-oral scene based on said three-dimensional relative positions.

BRIEF DESCRIPTION OF THE DRAWINGS

The invention is herein described, by way of example only, with reference to the accompanying drawings, wherein.

DESCRIPTION OF THE PREFERRED EMBODIMENTS

The principles and operation of a method according to the present invention may be understood with reference to the drawings and the accompanying description.

Figure 2A:
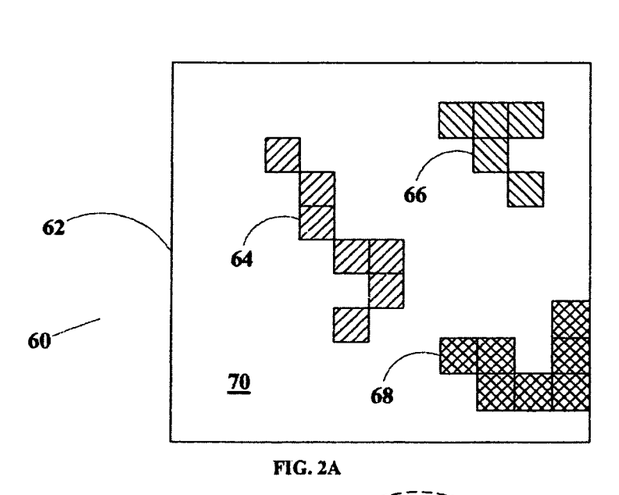
FIG. 2A illustrates examples of random patterns for structured illumination according to embodiments of the present invention.
Figure 2B:
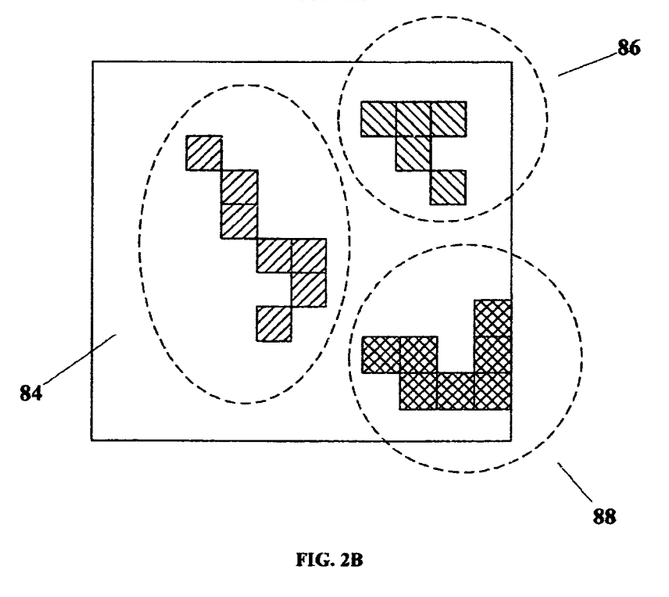
FIG. 2B illustrates the examples of FIG. 2A as detected patterns according to embodiments of the present invention.

In accordance with the present invention, structured illumination containing stored random patterns is used to convey surficial features to an intra-oral scene to be modeled in three dimensions by a single image, wherein triangulation is performed relative to a stored image of the structured illumination impinging from a different angle on a known surface, such as a plane. The method of the invention can be applied in various dental applications and fields, as well as be put to use in dental veterinary practice, and forensic dental medicine. In a preferred embodiment of the present invention, the light projected on the site of interest within the mouth bears randomly-structured and randomly-distributed patterns such that each projected pattern is probabilistically unique over the entire area onto which the light has been projected. To illustrate the method of the invention reference is made to FIG. 2A and FIG. 2B. An acquired image 60 is bounded by boundary line 62. Within image 60, several distinct pixel aggregates 64, 66, and 68 are apparent, such that each aggregate forms a distinct pattern which is different from the other patterns, and also being distinctly different from a background 70. In FIG. 2B, a pattern 84 is now defined as a separate entity, delineated schematically by a dashed line ellipsoid. A pattern 86 is likewise defined and delineated, and a pattern 88 is a third pattern so delineated. It is once again noted that these patterns of the present invention are two-dimensional, in contrast to prior-art patterns, such as those of Corby, which are one-dimensional.

In accordance with the present invention, the saved random patterns are projected on the intra-oral scene to be modeled, such that the probability for a certain pattern to appear more than once on the projected area is extremely low. At the image level, a projected pattern is defined as a specific pattern of aggregated pixels. An additional aspect of certain embodiments of the present invention is that any pixel pattern is characterized not only by its form, i.e. the specific shapes formed by the pixels at each point, but also by the distribution (i.e., the order and relative proximity to other patterns) of the patterns within the structured illumination. Hence, the order and relative proximity to other patterns within the image can be used to distinguish points from one another and to properly match corresponding points in the different images. In particular, in certain embodiments of the present invention the patterns are randomly distributed over an intra-oral scene, in addition to being randomly shaped. The term "randomly distributed" herein denotes that a pattern itself, separate from shape thereof, has been generated with a random position in the intra-oral scene.

Thus in FIG. 2B, at the image level, pattern 84 (which is equivalent to pattern 64) lies to the left of pattern 86 (which is equivalent to pattern 66) and pattern 88 (which is equivalent to pattern 68) in a clockwise order. As can be seen, the identified patterns not only differ from each other, but also are distributed and have a spatial relationship with other patterns of the image.

When matching patterns corresponding to the same single point of the structured illumination are obtained in the image of the intra-oral scene and the reference image, triangulation can be performed to determine the z-axis position of the pattern. The x-y positions of the pattern can be obtained directly from the image. Together, the three-dimensional x-y-z position of the pattern can thus be obtained for 3D modeling.

One-Dimensional Random Patterns

Figure 3:
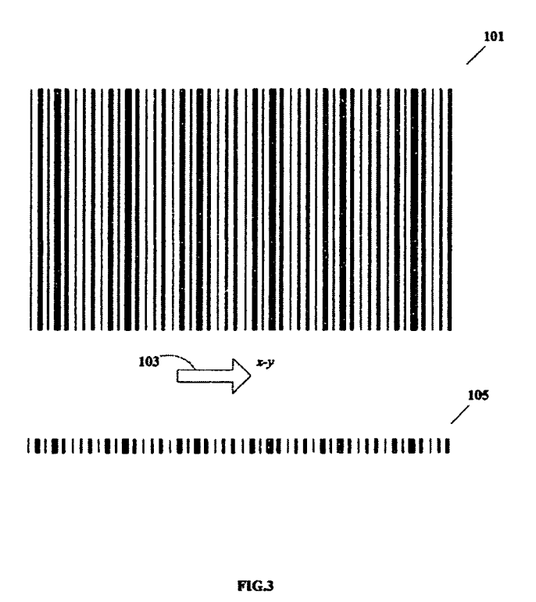
FIG. 3 illustrates examples of one-dimensional random patterns for structured illumination according to an embodiment of the present invention.

FIG. 3 illustrates an example of a randomly-generated pattern 101 whose random information content extends one-dimensionally in a direction 103 in the x-y plane. The pattern contains bands of varying width, similar to the familiar "bar code" patterns, except that the widths and spacing between the bands are assigned randomly. No random information is encoded perpendicular to direction 103. A narrow version of pattern 101 is shown in a pattern 105.

Although the restriction of encoding the random information in a single direction limits the amount of information that can be contained in the pattern, and thereby allows a higher probability of aliasing, this can be overcome by generating a continuous pattern, which permits continuous and uninterrupted tracking across the images. That is, this form of structured illumination is conducive to the projecting of a series of scanned lines over the intra-oral scene, rather than a grid of points. The information content in the lines can therefore be increased to achieve effective anti-aliasing.

In addition, there are certain advantages to restricting the information to a single direction in a manner as presented in FIG. 3. Because the information content is constrained to a direction parallel to the scan, the analysis and matching of corresponding patterns in the different images is simpler than for patterns of spots (such as illustrated in FIGS. 2A and 2B), where the information is two-dimensional. Thus, analysis is faster for the one-dimensional patterns as exemplified in FIG. 3.

Figure 4:
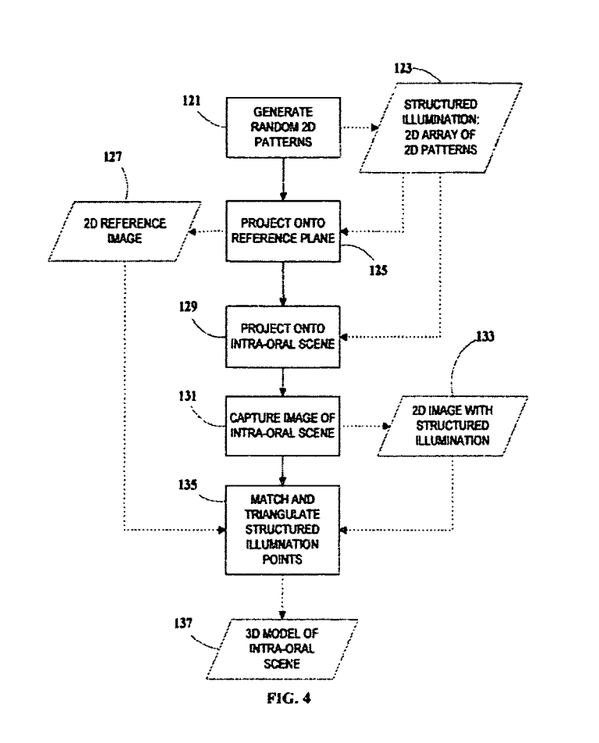
FIG. 4 is a flow-chart of a method for generating and storing structured illumination patterns and producing three-dimensional models of intra-oral scenes according to an embodiment of the present invention.

FIG. 4 is a flow-chart of a method according to an embodiment of the present invention, by which random patterns are generated and saved. In a step 121 two-dimensional random patterns are generated (as previously detailed) and are saved for use in structured illumination in a two-dimensional array 123. Array 123 may be saved utilizing photographic storage, such as in a slide which is suitable for projecting the array onto a surface.

Then, array 123 with the previously-described random patterns is projected onto a reference surface in a step 125 from a first angle relative to the reference surface. In an embodiment of the present invention, the reference surface is a plane. In another embodiment of the present invention, the reference surface is a general surface with a mathematical description An image of the structured illumination on the reference surface from the projection of array 123 is acquired and saved as a reference image 127.

Next, array 123 is projected at the previously-used first angle (see above) onto the intra-oral scene in a step 129. In a step 131, an image 133 of the intra-oral scene is captured from a second angle relative to the intra-oral scene. It is noted that image 133 contains the point locations where the projection of array 123 impinges on the surface of the intra-oral scene—that is, image 133 contains a two-dimensional image of the structured illumination on the surface of the intra-oral scene. Finally, in a step 135 the points of structured illumination of array 123 in image 133 are matched with the points of structured illumination of array 123 in reference image 127, and the z-axis positions of those points are computed by triangulation, using parallax measurements, to obtain a three-dimensional model 137 of the intra-oral scene.

Figure 5:
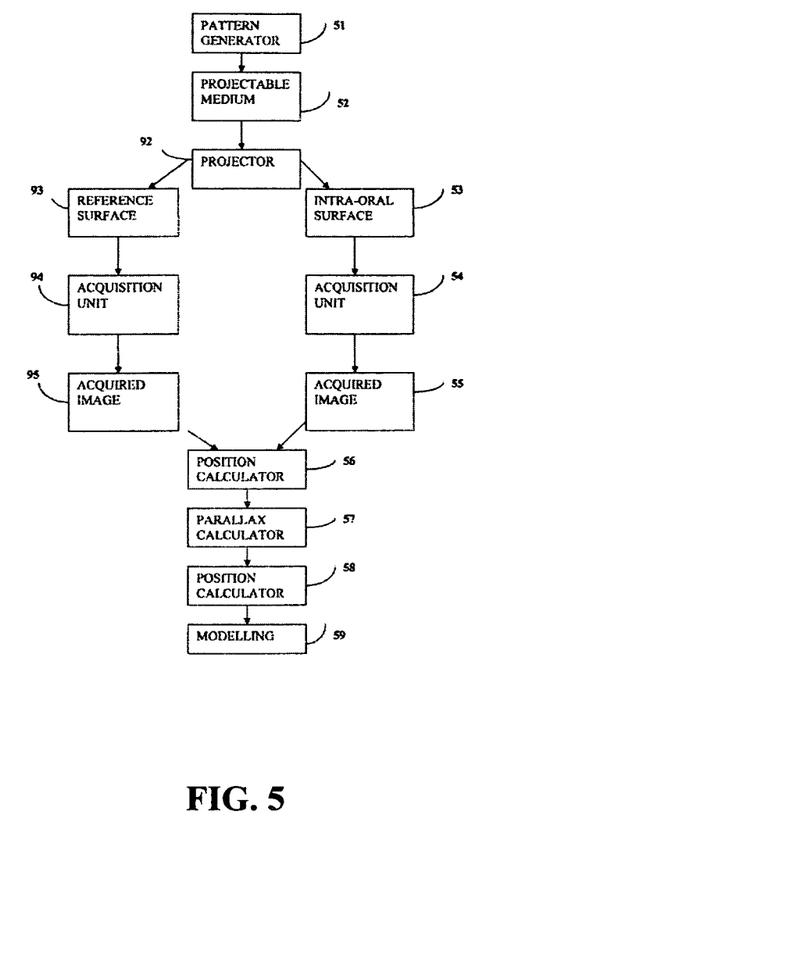
FIG. 5 is a block diagram illustrating a system according to an embodiment of the present invention.

FIG. 5 is a schematic representation of a system for three-dimensional modeling of the surface features of an intra-oral scene for a dental application, the system comprising a generator 51 for generating a two-dimensional array of a plurality of random, one or two-dimensional patterns. The pattern created is stored in a storage medium operative to allow projecting said array 52, and a first projector 92 for projecting said array from said projectable medium onto a reference surface 93 from a first angle. An acquisition unit 94 is a first acquiring means for acquiring a first image 95 of said array projected on said reference surface from a second angle. A second projector 92 is used for projecting said array from said projectable medium onto the intra-oral scene at said first angle and a second acquiring means, and acquisition unit 53 for acquiring a second image 55 of said array projected on the intra-oral scene from said second angle. A first position calculator 56 is used for calculating the two-dimensional relative positions of said random patterns based on the relative positions thereof in an image, and a pattern-matching means for matching said random two-dimensional patterns in said first image 95 with said random two-dimensional patterns in said second image 55. A parallax calculator 57 is used for calculating the parallax between said random patterns in said first image 95 with said random patterns in said second image 96. A second position calculator 58 is used for calculating three-dimensional relative positions of the random patterns based on the two-dimensional relative positions and said parallax, and a modeling means 59 for constructing a three-dimensional model of the intra-oral scene based on said three-dimensional relative positions. A system used by the user needs the reference image but not the means of generating the reference image.

Figure 6:
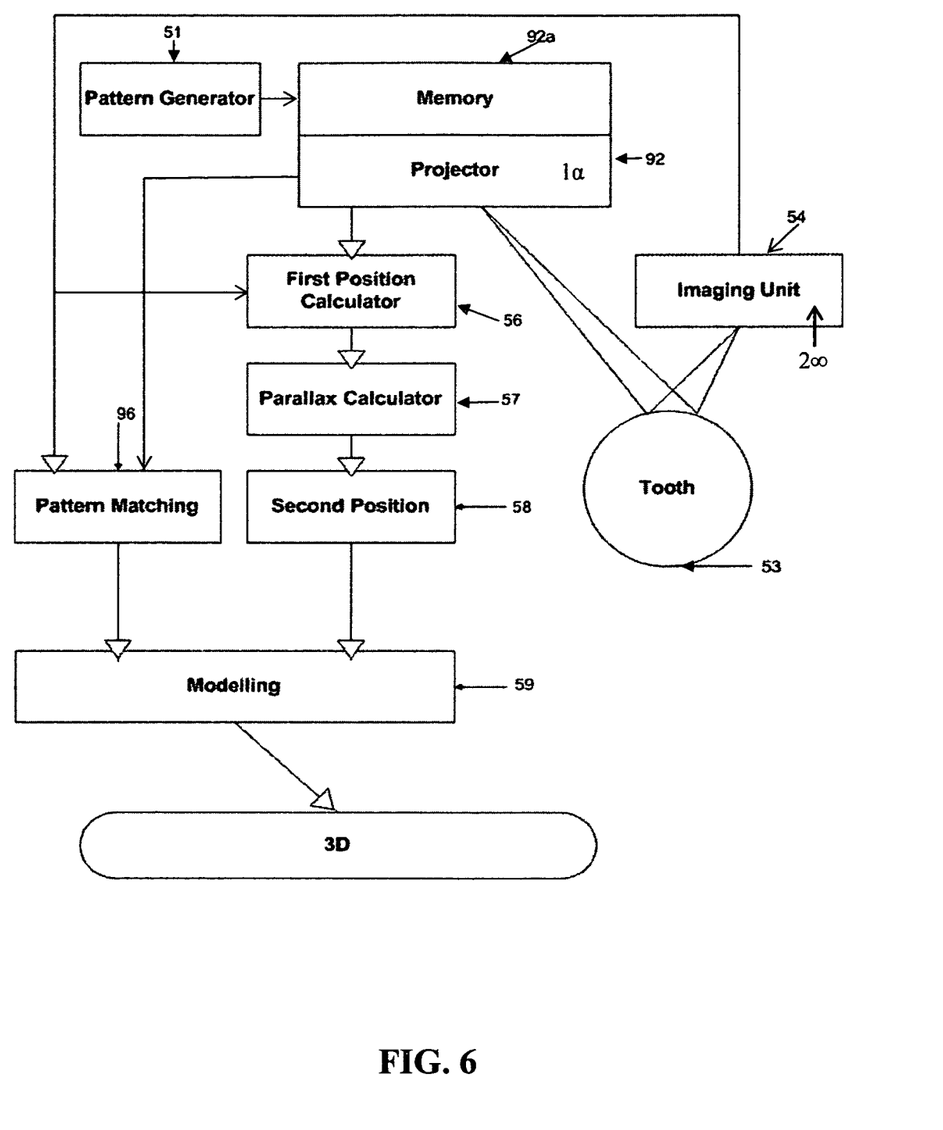
FIG. 6 illustrates a physical embodiment of the present invention.

FIG. 6 is a physical representation of a system for three-dimensional modeling of the surface features of an intra-oral scene for a dental application, the system comprising a generator 51 for generating a two-dimensional array of a plurality of random, one or two-dimensional patterns. The pattern created is stored in a storage medium 92a operative to allow projecting the array on the intra oral surface 53 from firs angle using a projector 92, the imaging unit 54 captures an image from second angle. The projector 92 provides information regarding the projected array and the projecting angle to the first position calculator 56 and the imaging unit 54 provides the captured image with the capturing angle to the first position calculator 56 that transfers the results to the parallax calculator 57. The parallax calculator 57 result is transferred to the second position calculator 58, which transfers the result to the modeling unit 59. The pattern matching unit 96 matches the projected array received from the projector 92 and the captured image that includes the array received from the imaging unit 54, the result is transferred to the modeling unit 59, which use the whole information to create a 3D model of the intra oral surface 53.

Multiple Imaging

Although the use of a single image is preferable in intra-oral use because of space constraints, it is also possible to use the present invention with multiple images as well. In this case, embodiments of the present invention utilize the above method for generating storable random structured illumination patterns as described herein, and then using those patterns with multiple-imaging techniques as exemplified in FIG. 1 and previously described.

Uses of the Invention

In dentistry, reconstitution of dental elements is a common practice. Projecting illuminated structures on intra oral objects to be modeled, can provide for an inexpensive yet advantageous background for a potentially efficacious 3D modeling of the oral cavity parts. Other applications for 3D mapping of intra-oral features include, but are not limited to: forensic dental medicine; insurance purposes; examination and treatment planning; and treatment automation. This particular invention is advantageous as it does not require a perfect projection on an ideal surface, and existing surficial features present on intra oral objects may even enhance the random surficial pattern.

While the invention has been described with respect to a limited number of embodiments, it will be appreciated that many variations, modifications and other applications of the invention may be made.

The invention claimed is:

1. A system for three-dimensional modeling of the surface features of an intra-oral scene for a dental application, the system comprising:
    a pattern generator for generating a two-dimensional array of a plurality of random two-dimensional or one-dimensional patterns;
    a projectable medium that contains a memory for storing said array, said memory operative to allow projecting said array;
    a projector for projecting said array from said memory onto the intra-oral scene at a first angle;
    an acquiring unit with at least one camera for acquiring images of said array projected on the intra-oral scene from a second angle;
    a first position calculator for calculating the two-dimensional relative positions of said random patterns based on the relative positions thereof in an image;
    a pattern-matching software for matching said random two-dimensional patterns in said first image with said random two-dimensional patterns in said second image;
    a parallax calculator for calculating the parallax between said random patterns in said first image with said random patterns in said second image;
    a second position calculator for calculating a three-dimensional relative positions of said random patterns based on said two-dimensional relative positions and said parallax; and
    a modeling software for constructing a three-dimensional model of the intra-oral scene based on said three-dimensional relative positions.

2. The system of claim 1, further includes a a reference surface on which a first image of said array is projected and wherein said acquisition unit has at least one camera for acquiring a second image of said array projected on the intra-oral scene from a second angle.

* * * * *

(12) EX PARTE REEXAMINATION CERTIFICATE (158th)
Ex Parte Reexamination Ordered under 35 U.S.C. 257

United States Patent
Ernst et al.

(10) Number: US 8,665,257 C1
(45) Certificate Issued: *Aug. 20, 2019

(54) THREE-DIMENSIONAL MODELING OF THE ORAL CAVITY

(75) Inventors: Maurice Moshe Ernst, Jerusalem (IL); Micha Geffen, Gillon (IL); Uri Neta, Coranit (IL); Carmi Cohen, Tel Adashim (IL)

(73) Assignee: DENSYS LTD

Supplemental Examination Request:
No. 96/000,269, Nov. 4, 2018

Reexamination Certificate for:
Patent No.: 8,665,257
Issued: Mar. 4, 2014
Appl. No.: 12/160,364
PCT Filed: Jan. 11, 2006
PCT No.: PCT/IL2006/000040
§ 371 (c)(1),
(2), (4) Date: Dec. 21, 2010
PCT Pub. No.: WO2007/080563
PCT Pub. Date: Jul. 19, 2007

(*) Notice: This patent is subject to a terminal disclaimer.

(51) Int. Cl.
*A61C 9/00* (2006.01)
*G16H 20/40* (2018.01)

(52) U.S. Cl.
CPC ............ *A61C 9/006* (2013.01); *G16H 20/40* (2018.01)

(58) Field of Classification Search
None
See application file for complete search history.

(56) References Cited

To view the complete listing of prior art documents cited during the supplemental examination proceeding and the resulting reexamination proceeding for Control Number 96/000,269, please refer to the USPTO's public Patent Application Information Retrieval (PAIR) system under the Display References tab.

*Primary Examiner* — Samuel G Rimell

(57) ABSTRACT

A method for creating three-dimensional models of intra-oral scenes features. The intra-oral scene is illuminated by a two-dimensional array of structured illumination points, with anti-aliasing achieved by using stored two-dimensional patterns of pixels for anti-aliasing. Using a single camera to form images reduces the amount of apparatus necessary to introduce into the patient's mouth. Three-dimensional models are obtained from the single image by triangulation with a stored image of the structured illumination onto a reference surface such as a plane. Alternative methods include the use of "bar-coded" one-dimensional patterns.

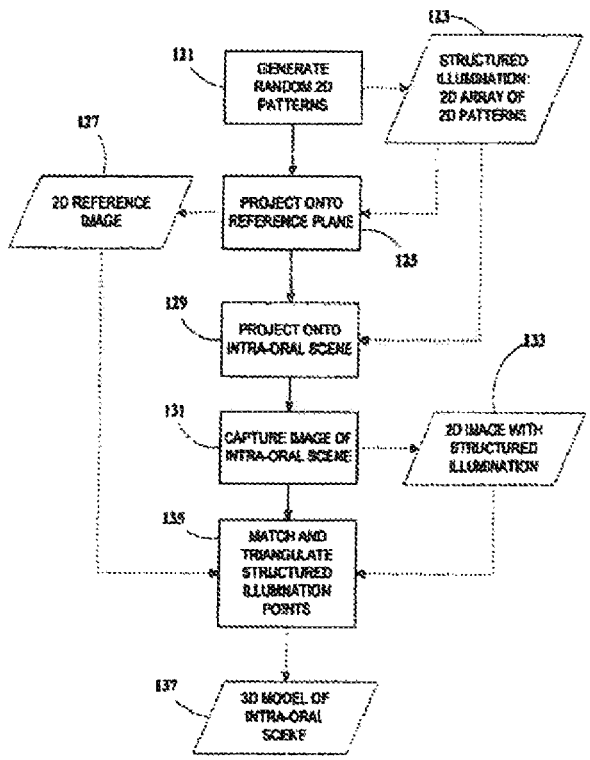

EX PARTE REEXAMINATION CERTIFICATE

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claim 1 is confirmed.

Claim 2 is determined to be patentable as amended.

New claims 3-5 are added and determined to be patentable.

2. The system of claim 1, further [includes] *including* a reference surface on which a first image of said array is projected and wherein said acquisition unit has at least one camera for acquiring a second image of said array projected on the intraoral scene from a second angle.

*3. The system of claim 1, wherein the plurality of random two-dimensional or one-dimensional patterns are randomly shaped.*

*4. The system of claim 1, wherein the plurality of random-two dimensional or one-dimensional patterns are randomly distributed.*

*5. The system of claim 1, wherein the plurality of random two-dimensional or one dimensional patterns are randomly shaped and randomly distributed.*

\* \* \* \* \*